United States Patent
Thorsen et al.

(10) Patent No.: US 11,235,109 B2
(45) Date of Patent: Feb. 1, 2022

(54) APPARATUS FOR HEATING SMOKABLE MATERIAL

(71) Applicant: BRITISH AMERICAN TOBACCO (INVESTMENTS) LIMITED, London (GB)

(72) Inventors: Mitchel Thorsen, Madison, WI (US); Roger Watkins, Madison, WI (US)

(73) Assignee: Nicoventures Trading Limited, London (GB)

(*) Notice: Subject to any disclaimer, the term of this patent is extended or adjusted under 35 U.S.C. 154(b) by 409 days.

(21) Appl. No.: 16/320,608

(22) PCT Filed: Jul. 24, 2017

(86) PCT No.: PCT/EP2017/068675
§ 371 (c)(1),
(2) Date: Jan. 25, 2019

(87) PCT Pub. No.: WO2018/019786
PCT Pub. Date: Feb. 1, 2018

(65) Prior Publication Data
US 2019/0166918 A1   Jun. 6, 2019

Related U.S. Application Data

(60) Provisional application No. 62/366,800, filed on Jul. 26, 2016.

(51) Int. Cl.
*A61M 11/04* (2006.01)
*A24F 40/50* (2020.01)
(Continued)

(52) U.S. Cl.
CPC .......... *A61M 11/042* (2014.02); *A24F 40/50* (2020.01); *A61M 16/109* (2014.02); *A24F 40/20* (2020.01); *A61M 15/06* (2013.01)

(58) Field of Classification Search
CPC ........ A24F 47/008; A24F 40/50; A24F 40/20; A61M 15/06; A61M 11/042; A61M 16/109
See application file for complete search history.

(56) References Cited

U.S. PATENT DOCUMENTS

2009/0090363 A1* 4/2009 Niland ................ A61M 16/122
128/203.26
2009/0223514 A1* 9/2009 Smith ................... A61M 16/16
128/203.14
(Continued)

FOREIGN PATENT DOCUMENTS

CN       104770895 A      7/2015
CN       205072071 U      3/2016
(Continued)

OTHER PUBLICATIONS

International Search Report and Written Opinion, Application No. PCT/EP2017/068675, dated Nov. 9, 2017, 15 pages.
(Continued)

*Primary Examiner* — Marcus E Harcum
(74) *Attorney, Agent, or Firm* — Patterson Thuente Pedersen, P.A.

(57) ABSTRACT

A method and apparatus for controlling a heater arrangement in a device arranged to heat smokable material is described. The method includes implementing a heater control loop, which control loop performs steps in one or more successive control periods. The control steps include determining a current remaining on time for a heating element of a heater arrangement based on the current rate of change of temperature, a target temperature and a current temperature of a zone of the device arranged to heat smokable material.

21 Claims, 12 Drawing Sheets

(51) Int. Cl.
*A61M 16/10* (2006.01)
*A24F 40/20* (2020.01)
*A61M 15/06* (2006.01)

(56) References Cited

U.S. PATENT DOCUMENTS

| | | | |
|---|---|---|---|
| 2011/0155718 A1 | 6/2011 | Greim et al. | |
| 2013/0298905 A1* | 11/2013 | Levin | A24F 40/00 128/202.21 |
| 2014/0060554 A1 | 3/2014 | Collett et al. | |
| 2014/0270727 A1 | 9/2014 | Ampolini et al. | |
| 2014/0345606 A1* | 11/2014 | Talon | A61M 11/042 128/202.21 |
| 2014/0360515 A1 | 12/2014 | Vasiliev et al. | |
| 2015/0165146 A1* | 6/2015 | Bowman | A61M 16/16 128/203.14 |
| 2015/0237916 A1 | 8/2015 | Farine et al. | |
| 2016/0088875 A1 | 3/2016 | Egoyants et al. | |
| 2016/0286865 A1* | 10/2016 | King | H05B 1/0297 |
| 2017/0231282 A1* | 8/2017 | Bowen | H05B 1/0227 131/329 |
| 2018/0000160 A1* | 1/2018 | Taschner | A24F 40/46 |
| 2018/0020728 A1* | 1/2018 | Alarcon | A24F 40/50 392/404 |
| 2019/0069599 A1* | 3/2019 | Monsees | A24F 40/51 |
| 2019/0314586 A1* | 10/2019 | Minskoff | A61M 11/02 |
| 2020/0221778 A1* | 7/2020 | Trzecieski | A24F 40/46 |

FOREIGN PATENT DOCUMENTS

| | | |
|---|---|---|
| EP | 2984946 A1 | 2/2016 |
| JP | 2015513922 A | 5/2015 |
| JP | 2015531600 A | 11/2015 |
| JP | 6273586 B2 | 2/2018 |
| WO | WO 2013/098397 | 7/2013 |
| WO | WO 2013098396 | 7/2013 |
| WO | WO 2013160112 | 10/2013 |
| WO | WO-2015193456 A1 | 12/2015 |

OTHER PUBLICATIONS

International Preliminary Report on Patentability for Application No. PCT/EP2017/068675, dated Nov. 29, 2018, 7 pages.
Office Action dated Mar. 17, 2020 for Japanese Application No. JP2019-501592, 4 pages.

* cited by examiner

APPARATUS FOR HEATING SMOKABLE MATERIAL

PRIORITY CLAIM

The present application is a National Phase entry of PCT Application No. PCT/EP2017/068675, filed Jul. 24, 2017, which claims priority from U.S. Provisional Application No. 62/366,800, filed Jul. 26, 2016, which is hereby fully incorporated herein by reference.

TECHNICAL FIELD

The present disclosure relates to apparatus arranged to heat smokable material.

BACKGROUND

Articles such as cigarettes, cigars and the like burn tobacco during use to create tobacco smoke. Attempts have been made to provide alternatives to these articles, which burn tobacco, by creating products that release compounds without burning. Examples of such products are so-called heat-not-burn products, also known as tobacco heating products or tobacco heating devices, which release compounds by heating, but not burning, the material. The material may be for example tobacco or other non-tobacco products or a combination, such as a blended mix, which may or may not contain nicotine.

SUMMARY

According to a first aspect of the present disclosure, there is provided a method of controlling a heater arrangement in an apparatus arranged to heat smokable material to volatize at least one component of the smokable material, the method comprising: implementing a heater control loop to control a heating element of the heater arrangement to heat a zone of the apparatus to a target temperature, wherein the control loop comprises, in one or more successive control periods, performing: determining a current temperature in the zone; determining a current rate of change of temperature in the zone; and determining a current remaining on time for the heating element of the heating arrangement to heat the zone to the target temperature based on the current rate of change of temperature, the target temperature and the current temperature of the zone.

According to a second aspect of the present disclosure, there is provided an apparatus configured to heat smokable material to volatize at least one component of the smokable material, the apparatus comprising: a heater arrangement comprising a heating element; a controller configured to implement a heater control loop to control the heating element of the heater arrangement to heat a zone of the apparatus to a target temperature, wherein the control loop comprises, in one or more successive control periods: determining a current temperature in the zone; determining a current rate of change of temperature in the zone; and determining a current remaining on time for the heating element to heat the zone to the target temperature based on the current rate of change of temperature, the target temperature and the current temperature of the zone.

According to a third aspect of the present disclosure, there is also provided a non-transitory computer-readable storage medium comprising a set of computer-readable instructions stored thereon, which, when executed by a processing system, cause the processing system to carry out a method of controlling a heater arrangement in an apparatus arranged to heat smokable material to volatize at least one component of the smokable material, the method comprising: implementing a heater control loop to control a heating element of the heater arrangement to heat a zone of the apparatus to a target temperature, wherein the control loop comprises, in one or more successive control periods, performing: determining a current temperature in the zone; determining a current rate of change of temperature in the zone; and determining a current remaining on time for the heating element of the heating arrangement to heat the zone to the target temperature based on the current rate of change of temperature, the target temperature and the current temperature of the zone.

BRIEF DESCRIPTION OF THE DRAWINGS

Embodiments of the disclosure will now be described, by way of example only, with reference to the accompanying drawings, in which.

DETAILED DESCRIPTION

Figure 1:
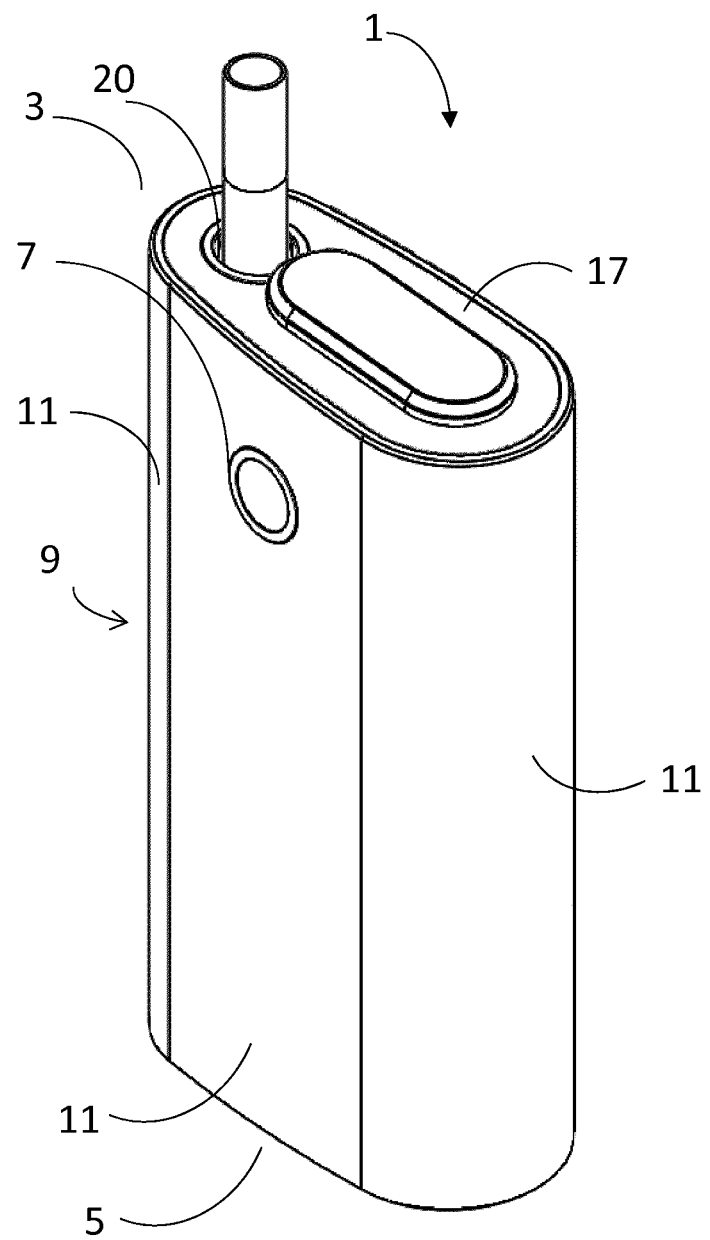
FIG. 1 shows a perspective view of an example of an apparatus for heating a smokable material.

As used herein, the term "smokable material" includes materials that provide volatilized components upon heating, typically in the form of an aerosol. "Smokable material" includes any tobacco-containing material and may, for example, include one or more of tobacco, tobacco derivatives, expanded tobacco, reconstituted tobacco or tobacco substitutes. "Smokable material" also may include other, non-tobacco, products, which, depending on the product, may or may not contain nicotine. "Smokable material" may for example be in the form of a solid, a liquid, a gel or a wax or the like. "Smokable material" may for example also be a combination or a blend of materials.

Apparatus is known that heats smokable material to volatilize at least one component of the smokable material, typically to form an aerosol which can be inhaled, without burning or combusting the smokable material. Such apparatus is sometimes described as a "heat-not-burn" apparatus or a "tobacco heating product" or "tobacco heating device" or similar. Similarly, there are also so-called e-cigarette devices, which typically vaporize a smokable material in the form of a liquid, which may or may not contain nicotine. The smokable material may be in the form of or provided as part of a rod, cartridge or cassette or the like which can be inserted into the apparatus. A heater for heating and volatilizing the smokable material may be provided as a "permanent" part of the apparatus or may be provided as part of the smoking article or consumable which is discarded and replaced after use. A "smoking article" in this context is a device or article or other component that includes or contains in use the smokable material, which in use is heated to volatilize the smokable material, and optionally other components.

Referring initially to FIGS. 1 to 4, there is shown an example of an apparatus 1 arranged to heat smokable material to volatilize at least one component of the smokable material, typically to form an aerosol which can be inhaled. The apparatus 1 is a heating apparatus 1 which releases compounds by heating, but not burning, the smokable material.

A first end 3 is sometimes referred to herein as the mouth or proximal end 3 of the device 1 and a second end 5 is sometimes referred to herein as the distal end 5 of the device 1. The apparatus 1 has an on/off button 7 to allow the apparatus 1 as a whole to be switched on and off as desired by a user.

The apparatus 1 comprises a housing 9 for locating and protecting various internal components of the apparatus 1. In the example shown, the housing 9 comprises a uni-body sleeve 11 that encompasses the perimeter of the apparatus 1, capped with a top panel 17 which defines generally the 'top' of the apparatus 1 and a bottom panel 19 which defines generally the 'bottom' of the apparatus 1. In another example the housing comprises a front panel, a rear panel and a pair of opposite side panels in addition to the top panel 17 and the bottom panel 19.

The top panel 17 and/or the bottom panel 19 may be removably fixed to the uni-body sleeve 11, to permit easy access to the interior of the apparatus 1, or may be "permanently" fixed to the uni-body sleeve 11, for example to deter a user from accessing the interior of the apparatus 1. In an example, the panels 17 and 19 are made of a plastics material, including for example glass-filled nylon formed by injection molding, and the uni-body sleeve 11 is made of aluminum, though other materials and other manufacturing processes may be used.

The top panel 17 of the apparatus 1 has an opening 20 at the mouth end 3 of the apparatus 1 through which, in use, a consumable article 21 containing smokable material may be inserted into the apparatus 1 and removed from the apparatus 1 by a user.

The housing 9 has located or fixed therein a heater arrangement 23, control circuitry 25 and a power source 27. In this example, the heater arrangement 23, the control circuitry 25 and the power source 27 are laterally adjacent (that is, adjacent when viewed from an end), with the control circuitry 25 being located generally between the heater arrangement 23 and the power source 27, though other locations are possible.

The control circuitry 25 may include a controller, such as a microprocessor arrangement, configured and arranged to control the heating of the smokable material in the consumable article 21 as discussed further below.

The power source 27 may be for example a battery, which may be a rechargeable battery or a non-rechargeable battery. Examples of suitable batteries include for example a lithium-ion battery, a nickel battery (such as a nickel-cadmium battery), an alkaline battery and/or the like. The battery 27 is electrically coupled to the heater arrangement 23 to supply electrical power when required and under control of the control circuitry 25 to heat the smokable material in the consumable (as discussed, to volatilize the smokable material without causing the smokable material to burn).

An advantage of locating the power source 27 laterally adjacent to the heater arrangement 23 is that a physically large power source 27 may be used without causing the apparatus 1 as a whole to be unduly lengthy. As will be understood, in general a physically large power source 27 has a higher capacity (that is, the total electrical energy that can be supplied, often measured in Amp-hours or the like) and thus the battery life for the apparatus 1 can be longer.

In one example, the heater arrangement 23 is generally in the form of a hollow cylindrical tube, having a hollow interior heating chamber 29 into which the consumable article 21 comprising the smokable material is inserted for heating in use. Different arrangements for the heater arrangement 23 are possible. For example, the heater arrangement 23 may comprise a single heating element or may be formed of plural heating elements aligned along the longitudinal axis of the heater arrangement 23. The or each heating element may be annular or tubular, or at least part-annular or part-tubular around its circumference. In an example, the or each heating element may be a thin film heater. In another example, the or each heating element may be made of a ceramics material. Examples of suitable ceramics materials include alumina and aluminum nitride and silicon nitride ceramics, which may be laminated and sintered. Other heating arrangements are possible, including for example inductive heating, infrared heater elements, which heat by emitting infrared radiation, or resistive heating elements formed by for example a resistive electrical winding.

In one particular example, the heater arrangement 23 is supported by a stainless steel support tube and comprises a polyimide heating element. The heater arrangement 23 is dimensioned so that, when the consumable article 21 is inserted in the apparatus 1, substantially the whole of the smokable material is heated in use.

The or each heating element may be arranged so that selected zones of the smokable material can be independently heated, for example in turn (over time) or together (simultaneously) as desired.

The heater arrangement 23 in this example is surrounded along at least part of its length by a thermal insulator 31. The insulator 31 helps to reduce heat passing from the heater arrangement 23 to the exterior of the apparatus 1. This helps to keep down the power requirements for the heater arrangement 23 as it reduces heat losses generally. The insulator 31 also helps to keep the exterior of the apparatus 1 cool during operation of the heater arrangement 23. In one example, the insulator 31 may be a double-walled sleeve which provides a low pressure region between the two walls of the sleeve. That is, the insulator 31 may be for example a "vacuum" tube, i.e. a tube that has been at least partially evacuated so as to minimize heat transfer by conduction and/or convection. Other arrangements for the insulator 31 are possible, including using heat insulating materials, including for example a suitable foam-type material, in addition to or instead of a double-walled sleeve.

The housing 9 may further comprises various internal support structures 37 (best seen in FIG. 4) for supporting all internal components, as well as the heating arrangement 23.

The apparatus 1 further comprises a collar 33 which extends around and projects from the opening 20 into the interior of the housing 9 and a generally tubular chamber 35 which is located between the collar 33 and one end of the vacuum sleeve 31.

Figure 2:
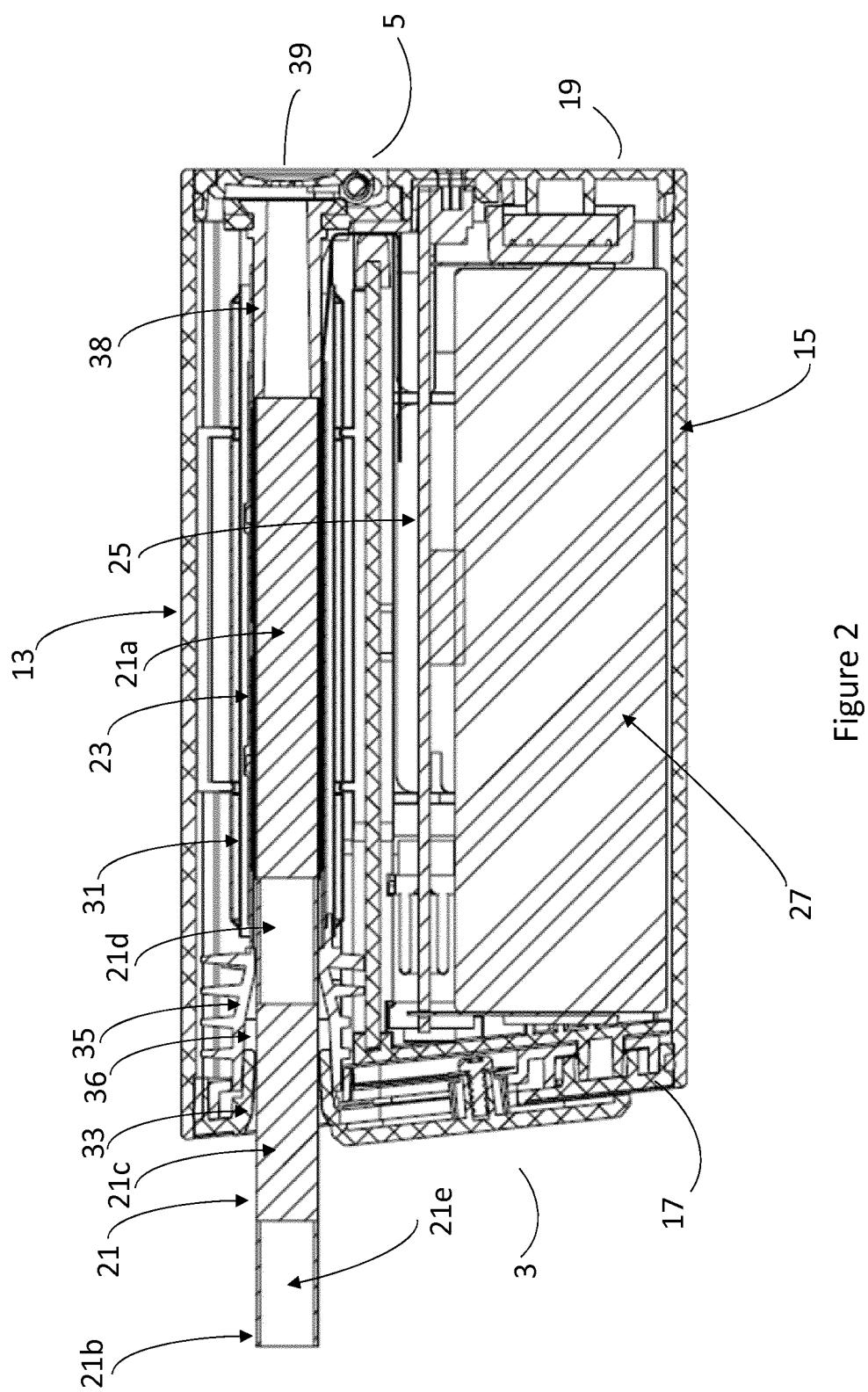
FIG. 2 shows a lateral cross-sectional view of the apparatus of FIG. 1 with a consumable article inserted.
Figure 3:
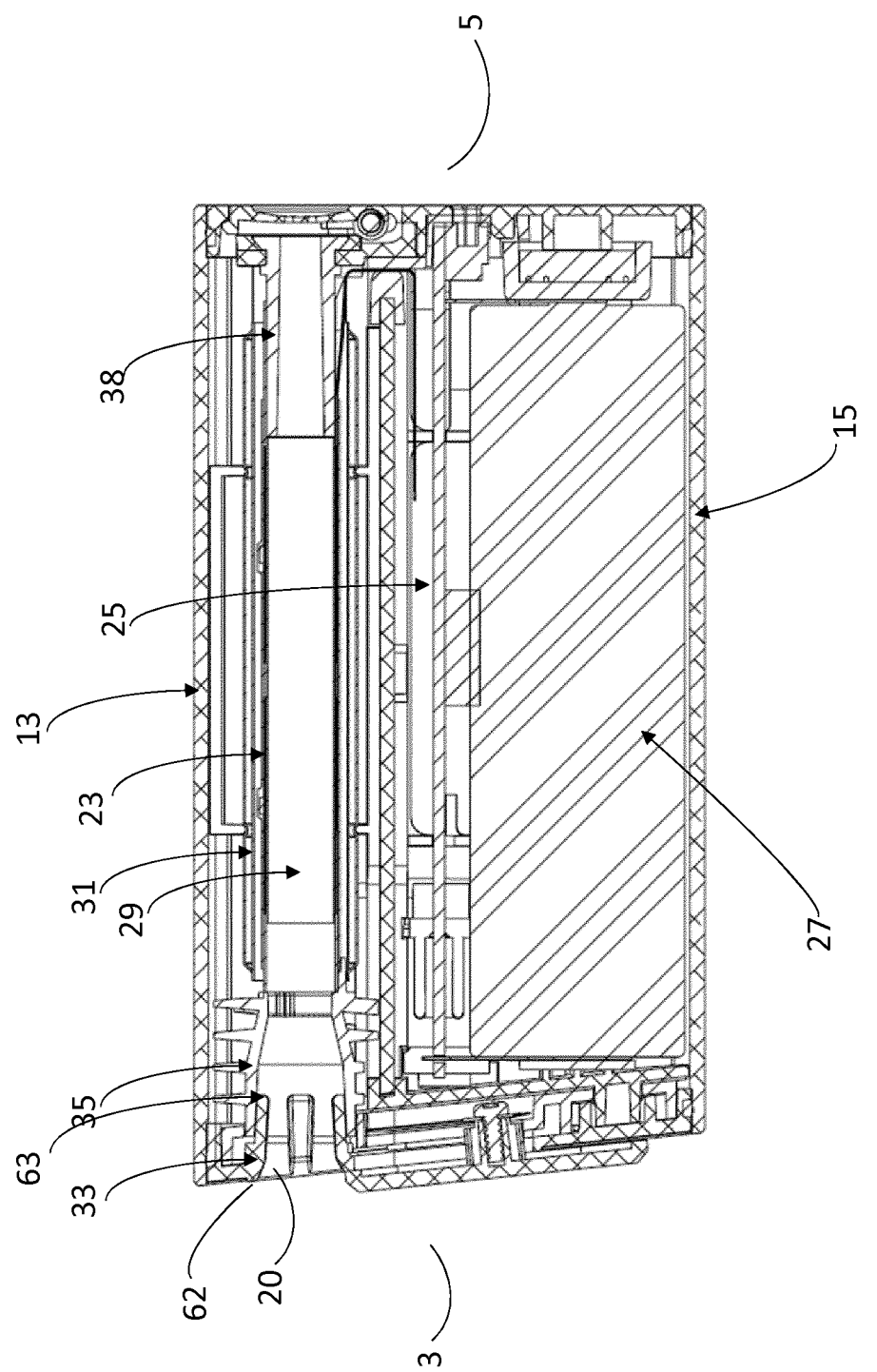
FIG. 3 shows a lateral cross-sectional view of the apparatus of FIG. 1 without a consumable article inserted.
Figure 4:
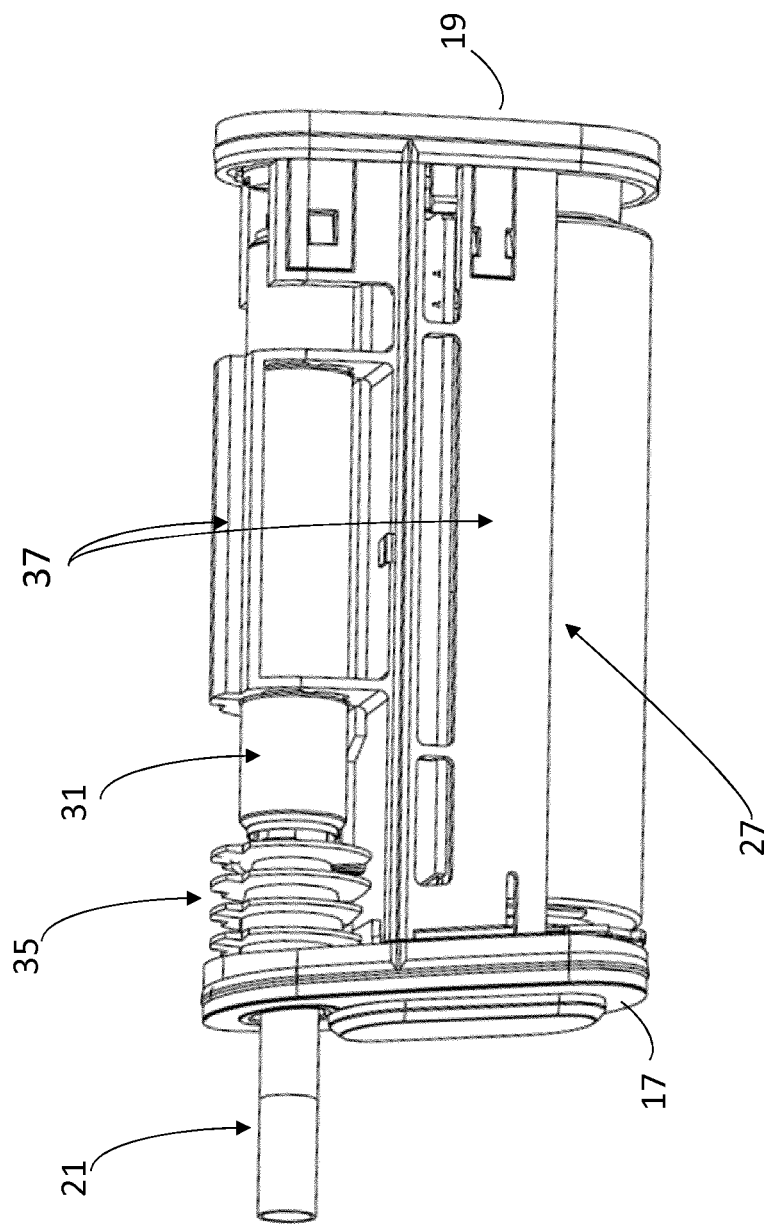
FIG. 4 shows a perspective side view of the apparatus of FIG. 1 with some external panels absent to show interior components of the apparatus.

One end of the chamber 35 connects to and is supported by the collar 33 and the other end of the chamber 35 connects to the one end of the vacuum sleeve 31 and hence supports the vacuum sleeve 31. Accordingly, as best seen in FIG. 3, the collar 33, the chamber 35 and the vacuum tube 31/heater arrangement 23 are arranged co-axially, so that, as best seen in FIG. 2, when the consumable article 21 is inserted in the apparatus 1, it extends through the collar 33 and the chamber 35 into the heater chamber 29.

As mentioned above, in this example, the heater arrangement 23 is generally in the form of a hollow cylindrical tube and this tube is in fluid communication with the opening 20 at the mouth end 3 of the device 1 via the chamber 35 and the collar 33.

Referring now to FIGS. 5a to 5d, in this example, the chamber 35 comprises a tubular body 35a that has a first open end 35b and a second open end 35c. The tubular body 35a comprises a first section 35d that extends from the first open end 35b to approximately half way along the tubular body 35a and a second section 35e that extends from approximately half way along the tubular body 35a to the second open end 35c. The first section 35d has a substantially constant internal diameter and the second section 35e has an internal diameter that tapers towards the second open end 35c.

The chamber 35 further comprises a cooling structure 35f, which in this example, comprises a plurality of cooling fins 35f spaced apart along the body 35a, each of which is arranged circumferentially around the body 35a.

The chamber 35 also comprises a flange portion 35g around the second open end 35c and a plurality of projections or clips 35h also arranged around the second open end 35c. Each clip 35h is generally "L" shaped and comprises a first portion 35h1 that is joined to the flange portion 35g and a second portion 35h2 that is generally perpendicular to first portion 35h1 and which extends in a direction generally parallel to the longitudinal axis of the tubular body 35a. Each second portion 35h2 comprises a stepped surface 35i that faces towards an axis that extends along the longitudinal axis of the tubular body 35a and which stepped surface 35i is slightly curved.

As best seen in FIG. 3, in this example, the chamber 35 is located in the housing 9 between the collar 33 and the vacuum tube 31/heater 23. More specifically, (i) at the second end 35c, the flange 35g butts an end portion of a polyimide tube of the heater arrangement 23 with the clips 35h resiliently engaging with the polyimide tube via their stepped surfaces 35i and the outer surfaces of the clips mating with an inside of the vacuum sleeve 31, and (ii) at the first open end 35b, the chamber 35 connects to the collar 33 by means of ridges 60, which form part of the collar 33 and project into the chamber 35. The ridges 60 are angled from a first end 62 of the collar 33 to a second end 63 of the collar towards an axis that extends along the longitudinal axis of the collar 33 and chamber 35. The ridges 60 lie flush with the internal surface of the chamber 35 to form a snug fit.

As is best appreciated from FIG. 2, the inner diameter of the first section 35d of the hollow chamber 35 is larger than the external diameter of the consumable article 21. There is therefore an air gap 36 between the hollow chamber 35 and the consumable article 21 when it is inserted in the apparatus over at least part of the length of the hollow chamber 35. The air gap 36 is around all of the circumference of the consumable article 21 in that region.

Figure 5B:
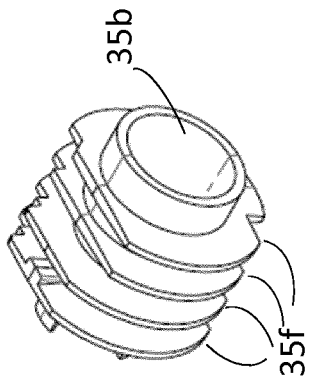
FIG. 5b shows a first perspective view of the internal component of the apparatus of FIG. 1.
Figure 5D:
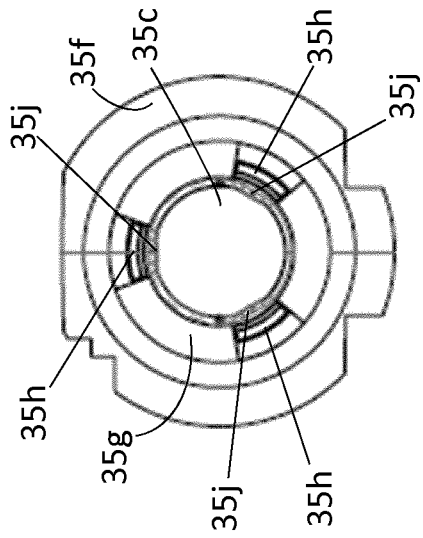
FIG. 5d shows an end view of the internal component of the apparatus of FIG. 1.
Figure 5A:
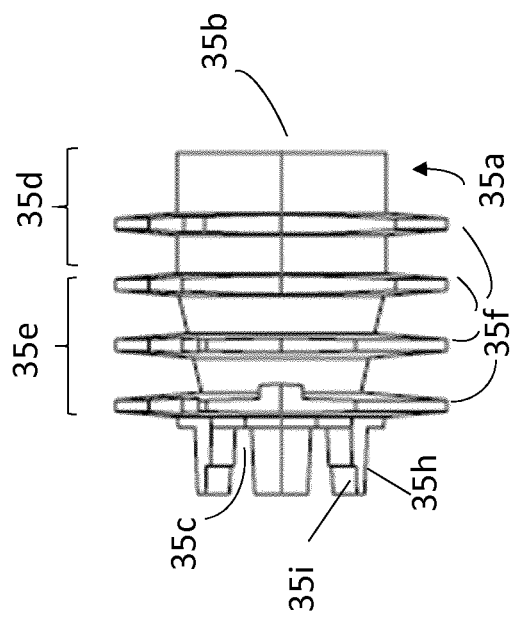
FIG. 5a shows a side view of an internal component of the apparatus of FIG. 1.
Figure 5C:
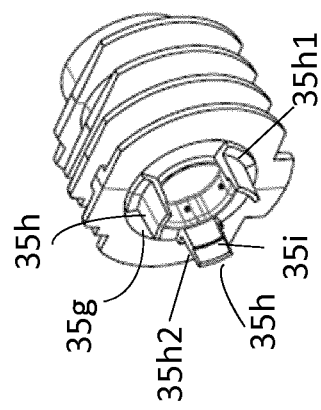
FIG. 5c shows a second perspective view of the internal component of the apparatus of FIG. 1.

As best seen in FIG. 5c and FIG. 5d, at the second open end 35c, the chamber 35 comprises a plurality (in this example 3) of small lobes or ridges 35j arranged circumferentially around an inner surface of the chamber 35 at the periphery of second open end 35c. Each of the lobes 35j extends a small distance in a direction parallel to the longitudinal axis of the chamber 35 and also extends a small amount radially at the second open end 35c. Together, the lobes 35j provide a gripping section that grips the consumable article 21 in order to correctly position and retain the portion of the consumable article 21 that is within the chamber 35 when the consumable article 21 is within the apparatus 1. Between them, the lobes 35j gently compress or pinch the consumable article 21 in the region or regions of the consumable article that are contacted by the lobes 35j. The lobes 35j may be comprised of a resilient material (or be resilient is some other way) so that they deform slightly (for example compress) to better grip the consumable article 21 when it is inserted in the apparatus 1 but then regain their original shape when the consumable article 21 is removed from the apparatus 1. The lobes 35j may be formed integrally with the chamber 35 or may be separate components that are attached within the chamber 35. The inner diameter around the lobes 35j may be, for example, 5.377 mm.

Figure 6:
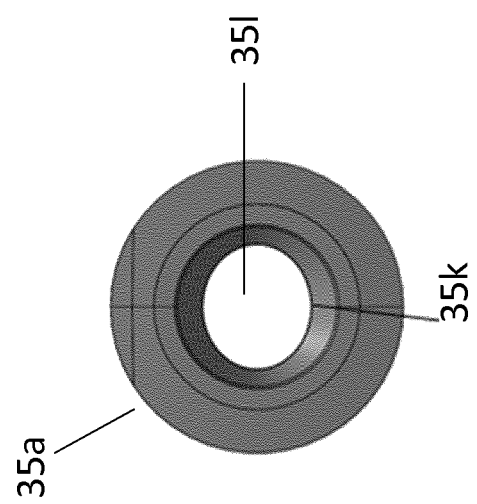
FIG. 6 shows an end view of an alternative internal component of the apparatus of FIG. 1.
Figure 7:
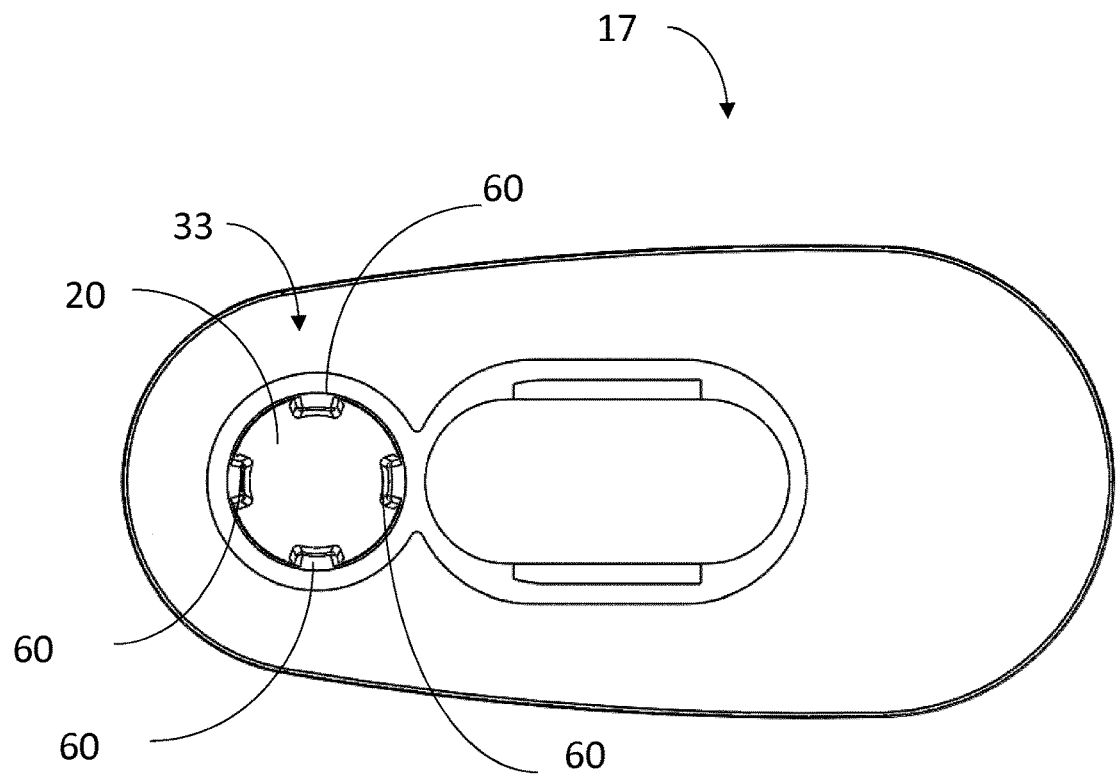
FIG. 7 shows a plan view of a front panel of the apparatus for heating a smokable material.

In an alternative example shown in FIG. 6, a resilient gripping section 35k within the hollow chamber 35 defines a substantially oval aperture 35l which, may extend along the longitudinal axis of the hollow chamber 35, and which when the consumable article 21 is inserted in the apparatus 1, gently compresses or pinches the section of the consumable article 21 that is in the oval aperture 35l so that this section of the consumable article 21 is deformed from being circular to being oval in cross section. In one example, the gripping section 35k is located towards the first open end 35b. In one example, the width of the oval section could be increased or decreased to increase or decrease the insertion/retention force. In a further example, small grooves (not shown) could be added in the surface of the oval aperture 35l that would interfere with the consumable article 21 rather than the entire surface area of the oval aperture 35l. This would minimize insertion/removal sensitivity to the transitions of the various consumable article components (tobacco, tipping paper, paper tube) passing through the gripping section 35k.

In a further example a combination of the lobes 35j and the oval gripping section 35k could be used to retain the consumable article 21 in the hollow chamber 35. For example, an oval gripping section 35k and the arrangement of lobes 35j could be spaced apart longitudinally in the hollow chamber 35 and act separately to retain an inserted consumable article 21 in place, or, the lobes 35j could be arranged around the surface of the oval gripping section 35k.

The chamber 35 may be formed of for example a plastics material, including for example polyether ether ketone (PEEK).

Referring again to FIGS. 2 to 4, in an example, the heating chamber 29 has a region 38 of reduced internal diameter towards the distal end 5. This region 38 provides an end stop for the consumable article 21 passed through the opening at the mouth end 3. This region 38 of reduced internal diameter, may for example, be provided by a hollow tube of the type described in detail in our U.S. Provisional Patent Application No. 62/185,227, filed on Jun. 26, 2015, the entire content of which is incorporated herein by reference.

The apparatus 1 may further comprise a door 39 at the distal end 5 that opens and closes an opening in the rear panel to provide access to the heating chamber 29 so that the heating chamber 29 can be cleaned. Examples of suitable doors are also discussed in more detail in U.S. Provisional Patent Application No. 62/185,227.

Referring now to FIGS. 7 to 10 in particular, there is shown an example of the top panel 17 of the apparatus 1. The top panel 17 generally forms the front end 3 of the housing 9 of the apparatus 1. The top panel 17 supports the collar 33 which defines an insertion point in the form of the opening 20 through which the consumable article 21 is removably inserted into the apparatus 1 in use.

The collar 33 extends around and projects from the opening 20 into the interior of the housing 9. In one example, the collar 33 is integral with the top panel 17 of the housing 9 so the collar 33 and the top panel 17 form a single piece. In an alternative example, the collar 33 is a distinct element from the top panel 17, but can be attached to the top panel 17 through an attachment, such as a locking mechanism, adhesive, or screws. Other attachments that are suitable for attaching the collar 33 to the top panel 17 may be used.

In this example, the collar 33 comprises a plurality of ridges 60 arranged circumferentially around the periphery of the opening 20 and which project into the opening 20. The ridges 60 take up space within the opening 20 such that the open span of the opening 20 at the locations of the ridges 60 is less than the open span of the opening 20 at the locations without the ridges 60. The ridges 60 are configured to engage with a consumable article 21 inserted into the apparatus 1 to assist in securing it within the apparatus 1.

In one example, the ridges 60 are circumferentially equally spaced around the periphery of the opening 20. In one example, there are four ridges 60, in other examples there may be more or fewer than four ridges 60.

Figure 10:
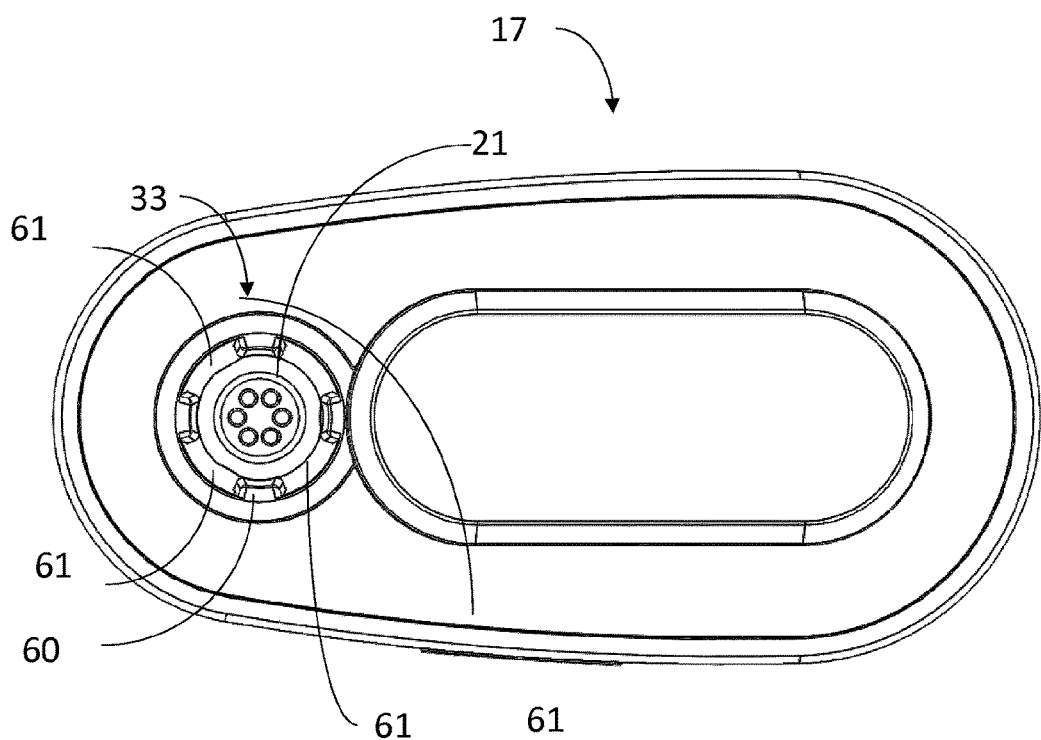
FIG. 10 shows a plan view of the front panel of FIG. 7 with a consumable article inserted.

FIG. 10 shows a plan view of the top panel 17 of the apparatus 1 with a consumable article 21 inserted into the opening 20. The ridges 60 project into the opening 20 to engage with the consumable article 21. The open spaces 61 defined by adjacent pairs of ridges 60 and the consumable article 21 form ventilation paths 61 around the exterior of the consumable article 21. These ventilation paths 61, as will be explained in more detail below, allow hot vapors that have escaped from the consumable article 21 to exit the apparatus 1 and allow cooling air to flow into the apparatus 1 around the consumable 21. The example in FIG. 10 shows four ventilation paths 61 located around the periphery of the consumable article 21, which provide ventilation for the apparatus 1 although there may be more or less such ventilation paths 61.

Figure 8:
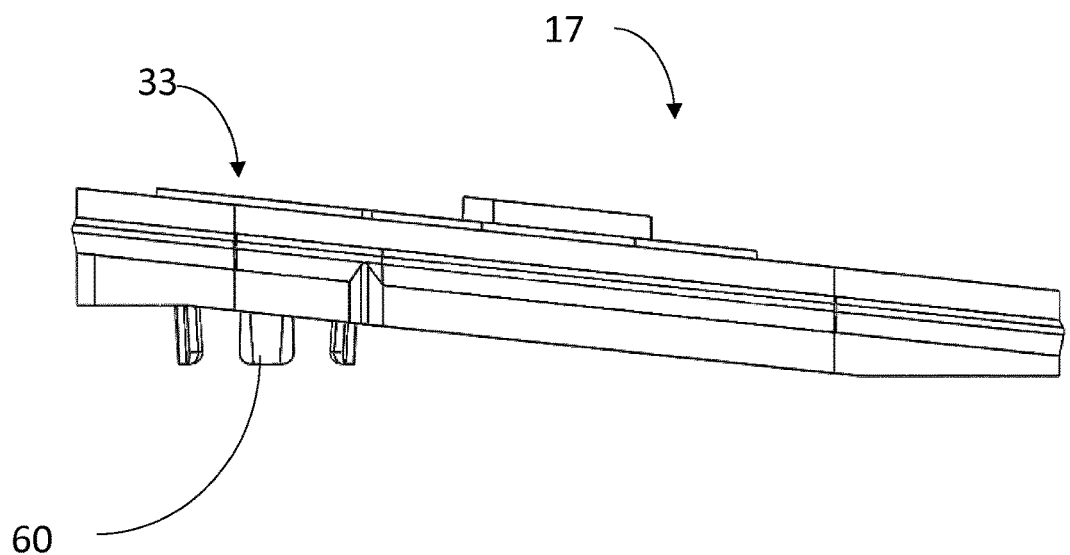
FIG. 8 shows a side view of the front panel of FIG. 7.
Figure 9:
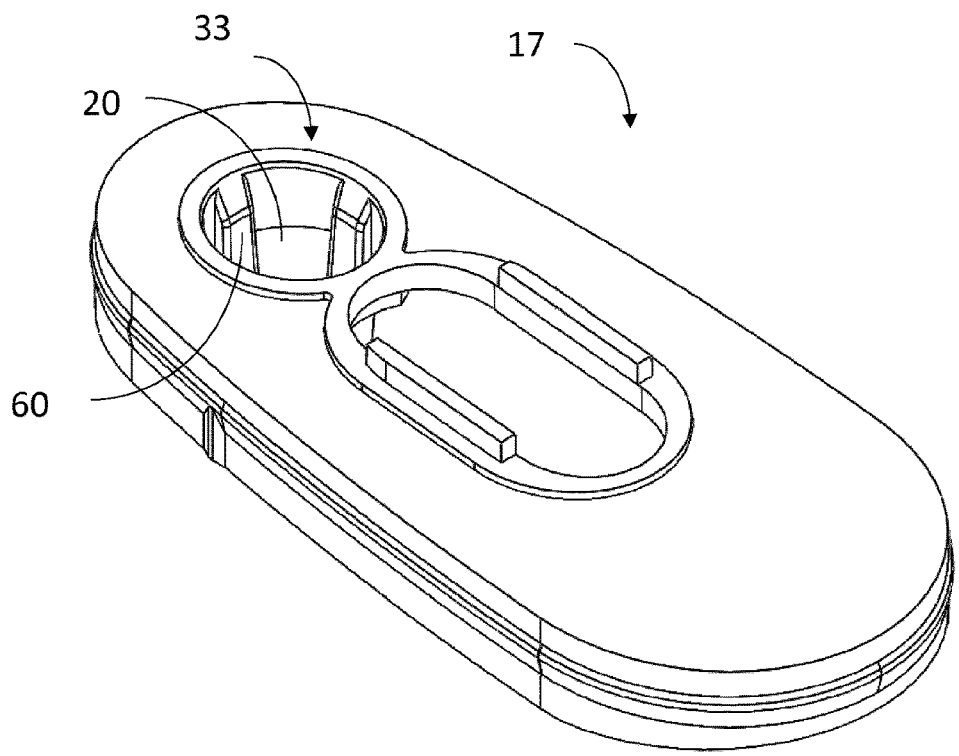
FIG. 9 shows a perspective view of the front panel of FIG. 7.

As mentioned above, the ridges 60 project radially into the opening 20 but, as best appreciated from FIG. 8, they also extend from the top panel 17 into the housing 9. The projection of the ridges 60 are angled towards each other, such that as the ridges 60 extend into the housing, the distance between the ridges 60 decreases. As best seen in FIG. 3, the projection of the ridges 60 into the housing enables the collar 33 to connect to the chamber 35 by means of the ridges 60 extending through the first open end 35b of the chamber 35 and engaging an inner wall of the chamber 35.

Referring again particularly to FIG. 2, in one example, the consumable article 21 is in the form of a cylindrical rod which has or contains smokable material 21a at a rear end in a section of the consumable article 21 that is within the heating arrangement 23 when the consumable article 21 is inserted in the apparatus 1. A front end of the consumable article 21 extends from the apparatus 1 and acts as a mouthpiece assembly 21b which includes one or more of a filter for filtering aerosol and/or a cooling element 21c for cooling aerosol. The filter/cooling element 21c is spaced from the smokable material 21a by a space 21d and is also spaced from the tip of mouthpiece assembly 21b by a further space 21e. The consumable article 21 is circumferentially wrapped in an outer layer (not shown). In one example, the outer layer of the consumable article 21 is permeable to allow some heated volatilized components from the smokable material to escape the consumable article 21.

In operation, the heater arrangement 23 will heat the consumable article 21 to volatilize at least one component of the smokable material 21a.

The primary flow path for the heated volatilized components from the smokable material 21a is axially through the consumable article 21, through the space 21d, the filter/cooling element 21c and the further space 21e before entering a user's mouth through the open end of the mouthpiece assembly 21b. However, some of the volatilized components may escape from the consumable article 21 through its permeable outer wrapper and into the space 36 surrounding the consumable article 21 in the chamber 35.

It would be undesirable for the volatilized components that flow from the consumable article 21 into the chamber 35 to be inhaled by the user, because these components would not pass through the filter/cooling element 21c and thus be unfiltered and not cooled.

Advantageously, the volume of air surrounding the consumable article 21 in the chamber 35 and the fin-cooled interior wall of the chamber 35 causes at least some of the volatilized components that escape the consumable article 21 through its outer layer to cool and condense on the interior wall of the chamber 35 preventing those volatilized components from being possibly inhaled by a user.

This cooling effect may be assisted by cool air that is able to enter from outside the apparatus 1 into the space 36 surrounding the consumable article 21 in the chamber 35 via the ventilation paths 61, which allows fluid to flow into and out of the apparatus 1. A ventilation path 61 will be defined between a pair of the plurality of neighboring ridges 60 to provide ventilation around the outside of the consumable article 21 at the insertion point.

In one example, a second ventilation path 61 is provided between a second pair of neighboring ridges for at least one heated volatilized components to flow from the consumable article 21 at a second location. Therefore ventilation is provided around the outside of the consumable article 21 at the insertion point by the first and second ventilation paths 61.

Furthermore, heated volatilized components that escape the consumable article 21 through its outer wrapper do not condense on the internal wall of the chamber 35 and are able to flow safely out of the apparatus 1 via the ventilation paths 61 without being inhaled by a user.

The chamber 35 and the ventilation both aid in reducing the temperature and the content of water vapor composition released in heated volatilized components from the smokable material.

Examples of a slope-based heater control scheme (control loop) will now be described in detail. The slope-based heater control loop may be implemented by a controller included in the control circuitry 25 in order to control the operation of the heater arrangement 23 to heat a zone of the heating chamber 29.

As described above, the heater arrangement 23 may be formed of plural heating elements. The different heating elements of the heating arrangement 23 may be controlled individually by the controller.

Figure 11:
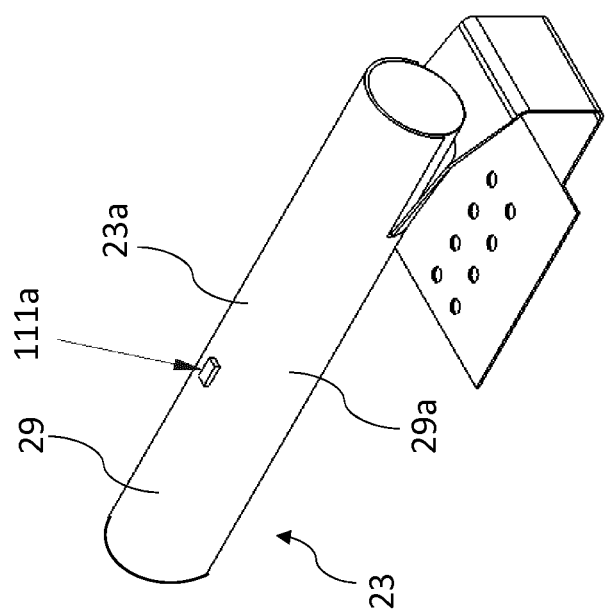
FIG. 11 shows a perspective view of a heating arrangement of the apparatus for heating a smokable material.

Referring now to FIG. 11, in this example, the heater arrangement 23 includes a heating element 23a and the heating chamber 29 comprises a heating zone 29a that is heated by the heating element 23a. In this example, the heating element 23a operates to heat the smokable material positioned within heating zone 29a. The heating element 23a has a corresponding temperature sensor 111a associated with it. In this example, the controller uses temperature measurements from the sensor 111a to control the operation of the heating element 23a.

In this example, the heating element 23a is configured to increase its temperature, and thereby increase the temperature within the heating zone 29a when it is operating. The state in which the heating element 23a is operating is referred to as the state in which the heating element 23a is on. Conversely, when the heating element 23a is not operating, it is referred to as being off. A duration of time during which the heating element 23a is switched on will hereafter be referred to as the heating element on duration.

In this example, the controller implements control of the heating element 23a by controlling a switch (not shown) configured to turn the heater on or off.

The temperature sensor 111a used for the slope-based heater control loop may be any suitable temperature sensor. In one example, the temperature sensor 111a is a resistance temperature detector or a thermocouple. In one example, the temperature sensor 111a is a sensor capable of detecting temperatures at least up to 300° C.

In this example the controller is in data communication with the temperature sensor 111a, and is configured to acquire temperature measurements from the temperature sensor 111a within the heating element 23a. The controller determines the current temperature of the zone 29a by acquiring temperature measurements from the temperature sensor 111a at first given intervals of time. In this example, the first given intervals of time are regular intervals of time. In a specific example, the controller acquires temperature measurements from the temperature sensor 111a every, for example, 10 ms. Any regular intervals of time other than 10 ms are possible. In other examples, the first given intervals of time are irregular intervals of time. In one example, the controller acquires a number of temperature measurements with a measurement acquired every 10 ms, and ceases to acquire any further temperature measurements until a time substantially later than 10 ms after the latest temperature measurement.

Hereinafter, in this example, it is assumed that the first given intervals of time, that is the intervals of time at which the controller monitors the temperature measured by the temperature sensor 111a, are regular intervals of time lasting 10 ms.

The first given intervals of time define the frequency with which the controller acquires temperature measurements from the temperature sensor 111a. That is, the frequency with which the temperature within the heating zone 29a is determined.

In one example, the controller calculates the rate of change of temperature with time, in other words a "temperature slope," based on a plurality of the temperature measurements acquired at first given intervals of time from the temperature sensor 111a. The temperature slope is calculated using temperature measurements acquired when the heating element 23a is switched on. This calculated temperature slope corresponds to the rate of change of temperature in the heating zone 29a when the heating element 23a is on. In this example, the controller calculates the temperature slope based on two temperature measurements. If the heating element on duration is 300 ms, the controller may use the temperature measurement acquired at the start of this 300 ms duration, and the measurement acquired at the end of the 300 ms duration in order to calculate the temperature slope. In other examples, the controller calculates the temperature slope within any suitable interval of time during the heating element on duration. In this example, the controller determines the current rate of change of temperature in the zone 29a by using temperature measurements acquired from the temperature sensor 111a during the latest heating element on duration.

In this example, the controller calculates the slope using the following formula:

$$\text{Calculated slope} = \frac{(T_2 - T_1)}{(t_2 - t_1)} \quad (1)$$

wherein $T_2$ represents the temperature measurement acquired at a time denoted by $t_2$ and $T_1$ represents the temperature measurement acquired at a time denoted by $t_1$ (where $t_2$ is a later time than $t_1$). In the example in which $(t_2-t_1)$ is an interval of time during the heating element on duration, the calculated slope provides an indication of the rate of change of temperature the heating element 23a is capable of achieving when switched on.

In one example, the controller sets a temperature set point which is a target temperature at which the heating zone 23a is desired to be during a session of use of apparatus 1. This target temperature may depend on how the smokable material 21a within the heating zone 29a is to be heated. In this example, the temperature set point is a temperature between 160° C. and 240° C. The controller may also vary the temperature set point during a session of use of the apparatus 1.

In this example, at the start of a session of use of the apparatus 1, the controller sets a temperature set point between 160° C. and 240° C., and switches the heating element 23a on. Once the heating element 23a is switched on, the controller repeatedly determines the current temperature of the zone 29a and the current temperature slope in the zone 29a as described above.

In this example, if the current temperature is less than the target temperature, the controller then calculates a total desired heating element on duration, in other words, a remaining on time for the heating element 23a for which the heating element 23a should be switched on in order to reach the target temperature using the current temperature slope and the current temperature in the zone 29a. In other words, the remaining on time is a time that the heating element 23a needs to be operated in order to achieve a change in temperature from the current temperature to the temperature set point. In this example, the current temperature is taken to be the latest temperature measurement acquired by the controller from the temperature sensor 111a.

The remaining on time may be calculated by setting the slope expected to be achieved when the heating element 23a is on, to the calculated slope calculated as described above using temperature measurements obtained by the controller from the temperature sensor 111a during a time when the heating element 23a was switched on.

The remaining on time may be denoted as $t_{on} = t_{target} - t_c$ wherein $t_c$ denotes the current time and $t_{target}$ denotes the time at which the temperature set point/target temperature is expected to be reached. The following formulas may be used to calculate the remaining on time that is expected to result in the target temperature being reached:

$$\frac{(T_{target} - T_c)}{(t_{off} - t_c)} = \frac{(T_2 - T_1)}{(t_2 - t_1)} \quad (2)$$

$$t_{on} = \frac{(t_2 - t_1) \times (T_{target} - T_c)}{(T_2 - T_1)} \quad (3)$$

In the above formulas, $T_c$ denotes the measured temperature at time $t_c$ and $T_{target}$ is the temperature set point/target temperature expected to be reached at a time $t_{off}$ after time $t_c$. The subscript "c" indicates that $T_c$ and $t_c$ relate to the current temperature of the zone 29a, and the current time respectively.

In this example, the controller implements the slope-based heater control loop by repeatedly performing the steps of determining the current temperature $T_c$ of the heating zone 29a, determining the current temperature slope of the zone 29a, and if the current temperature $T_c$ is below the target temperature $T_{target}$, determining the remaining on time $t_{on}$ for the heating element 23a as described above. These steps hereafter will be referred to as the control steps.

In one example, the controller repeats the above described steps at second given intervals of time. In this particular example, the controller performs these steps every 300 ms. The second given intervals of time therefore define control periods of the slope-based heater control loop. It will be understood that the second given intervals of time (the control period), in most examples, will be greater than the first given intervals of time at which the controller acquires temperature measurements from the temperature sensor 111a.

In this example, the controller is configured to control the heating element 23a to be on for the determined remaining on time $t_{on}$. If the determined remaining on time $t_{on}$ is greater than the control period, the heating element 23a is kept on for the entire duration of the control period, and at the end of the control period, the controller repeats the control steps. However, if the remaining on time $t_{on}$ expires within the control period, the controller switches the heating element 23a off. For example, if the control period is 300 ms long, and the determined remaining on time $t_{on}$ is 200 ms, the controller switches the heating element 23a off once the 200 ms heating element on duration has expired during the 300 ms control period. Within this 300 ms interval therefore, the heating element is switched on for part of the interval, but switched off for another part of the same interval. At the end of such a control period, and at the start of the subsequent control period, the controller determines a current temperature $T_c$, and if the current temperature $T_c$ is less than the target temperature $T_{target}$, the controller turns the heating element 23a back on and calculates a remaining on time based on the current temperature slope, current temperature $T_c$ and the target temperature $T_{target}$. Thereafter, since the heater is switched on, the controller controls the operation of the heating element 23a by applying the control steps described above.

The above implementation of the slope-based control loop has the effect of slowing the change of temperature of the zone 29a down as the target temperature is approached. When the remaining on time $t_{on}$ becomes shorter than the control period, the change of temperature of the zone 29a with time becomes slower than the temperature slope due to the heating element 23a being switched off for part of the control period. In this way, the target temperature $T_{target}$ is reached without a large overshoot of the temperature $T_c$ above the target $T_{target}$.

In this example, once the target temperature $T_{target}$ is reached, the controller implements a hold temperature mode, in which mode the controller controls the heating element 23a in order to maintain the zone 29a at the target temperature $T_{target}$. The controller switches the heating element 23a off when the current temperature $T_c$ is equal to or above the target temperature $T_{target}$. In hold temperature mode, the controller turns the heating element 23a on if in addition to the current temperature $T_c$ being at least a first temperature threshold value below the set point $T_{target}$, one or more of the below listed conditions are met:

(i) The current temperature $T_c$ is lower than the previous temperature measurement;
(ii) A time greater than a first time threshold has expired since the heating element 23a was turned off and the current temperature $T_c$ is at least a second temperature threshold below the target temperature $T_{target}$; and
(iii) A time greater than a second time threshold has expired since the heating element 23a was turned off.

In one example, the first temperature threshold may be 1° C. such that the controller turns the heating element 23a on if the current temperature $T_c$ is more than 1° C. below the set point $T_{target}$ and the current temperature $T_c$ is lower than the previous temperature measurement. In an example, the first time threshold may be 300 ms and the second temperature threshold may be 10° C. such that if a time greater than 300 ms has elapsed since the heating element 23a was turned off and the current temperature is at least 10° C. below the set point $T_{target}$, the controller may turn the heating element 23a on. In one example, the second time threshold may be 500 ms such that if a time greater than 500 ms has expired since the heating element 23a was turned off and the necessary condition of the temperature being at least 1° C. below the set point $T_{target}$ is met, the controller may turn the heating element 23a on. The controller may thus maintain the current temperature substantially at the temperature set point in hold temperature mode. That is, the controller is configured to maintain the temperature threshold once it is reached. It will be understood that each time the heating element 23a is turned on, the controller performs the control steps and implements the slope-based control loop.

During operation of the apparatus 1, the controller may change the target temperature $T_{target}$ as previously mentioned. In one example, the controller changes the target temperature $T_{target}$ in accordance with a desired temperature profile, the temperature profile being temperature as a function of time (a temporal temperature profile). In another example, the controller changes the target temperature $T_{target}$ based on various other factors, for example, the time elapsed since the start of the session of use of the smokable material heating device 1, the amount of smokable material remaining in the chamber 29 and the like.

If the controller increases the target temperature $T_{target}$ and the current temperature $T_c$ is less than the target temperature $T_{target}$, in this example, the controller turns the heating element 23a on and uses the slope-based control scheme described above in order to reach the target temperature $T_{target}$. If on the other hand, the controller decreases the target temperature $T_{target}$, the heating element 23a is turned off until the temperature $T_c$ falls below the new set point $T_{target}$, after which the heating element 23a is turned on based on the above described list of conditions for the heater being turned on during hold temperature mode are met.

Figure 12:
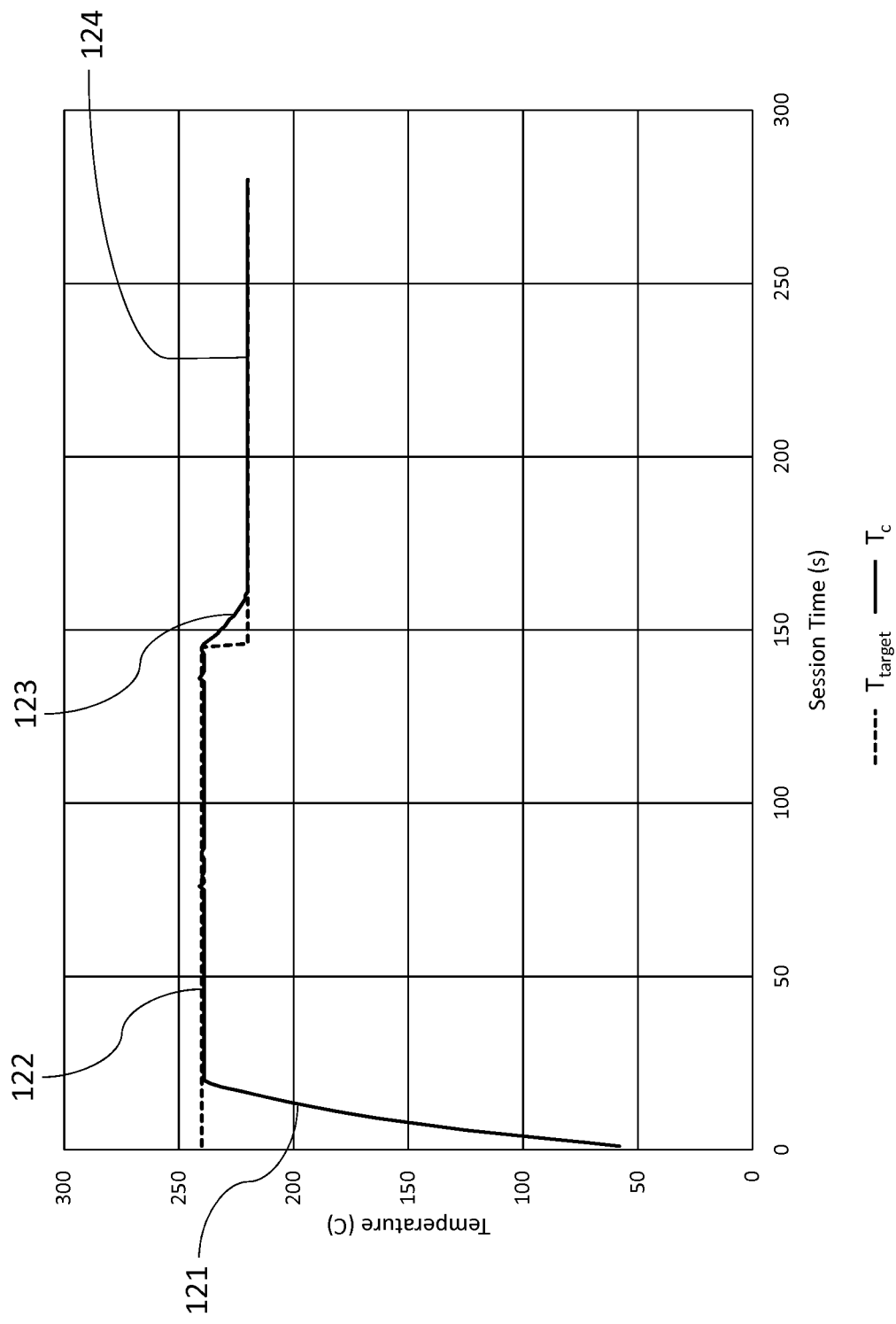
FIG. 12 shows a graph showing the time evolution of a target and corresponding measured temperature within the heating arrangement of FIG. 11.
Figure 13:
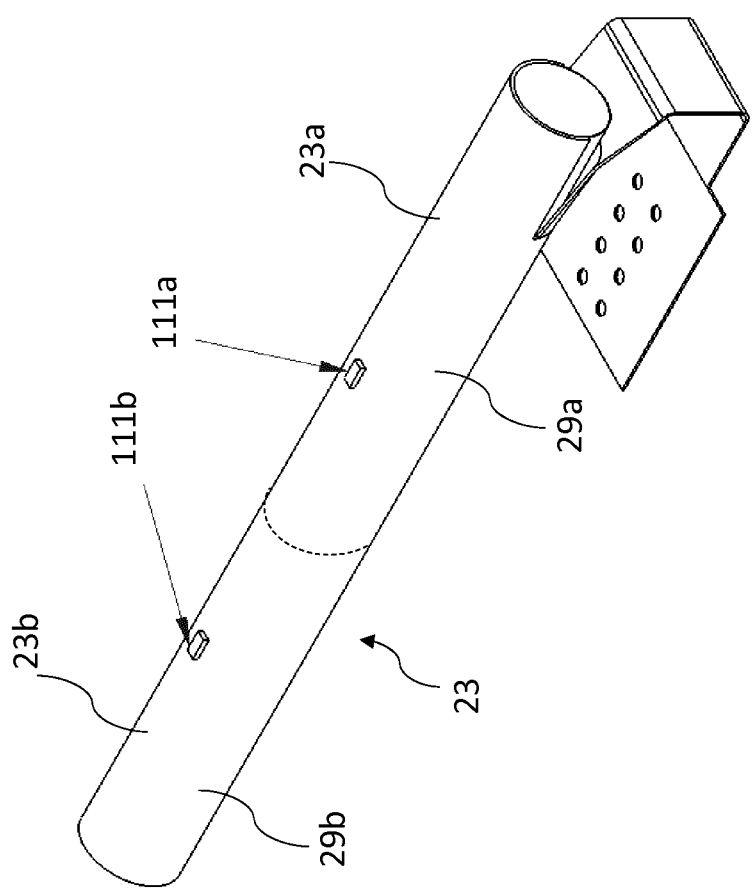
FIG. 13 shows a perspective view of an alternative heating arrangement of the apparatus for heating a smokable material.

A specific example of the slope-based heater control will now be described with reference to FIG. 12. FIG. 12 shows the target temperature $T_{target}$ of a heating element 23a as a function of time, and the current temperature $T_c$ acquired by the controller from a temperature sensor 111a as a function of time. The controller acquires temperature measurements from the temperature sensor every 10 ms. At the start of a session of use of the apparatus 1, the heater is switched on to heat the smokable material 21a in the heating zone 29a. In this example, the target temperature $T_{target}$ is set to 240° C. The temperature acquired by the controller from the temperature sensor 111a at a session time of 0 s is 72° C. The controller implements the slope-based heater control in order to reach the target temperature $T_{target}$. The part 121 of the measured temperature $T_c$ illustrates the temperature change towards the set point during implementation of the slope-based control. As the measured temperature $T_c$ approaches the target temperature $T_{target}$, the overall change of the measured temperature $T_c$ with session time of the heating zone 23a can be seen to decrease as a result of the determined remaining on time $t_{on}$ becoming shorter than the control period, of 300 ms in this example, as the target temperature $T_{target}$ is approached. This can most easily be seen at the part 121 of the measured temperature $T_c$ in FIG. 12 close in temperature to the target temperature $T_{target}$ of 240° C. In other words the time evolution of the measured temperature $T_c$ flattens as $T_c$ approaches the target temperature $T_{target}$. Part 122 of the measured current temperature $T_c$ illustrates the controller maintaining the temperature at the target temperature $T_{target}$ of 240° C. in hold temperature mode. At a time of 145 seconds after the start of the operation of the apparatus 1, the controller lowers the target temperature $T_{target}$ to 220° C. The controller then switches the heating element 23a off and the measured current temperature $T_c$ lowers with time as shown at 123 until the measured current temperature $T_c$ is below the new lower target temperature $T_{target}$ of 220° C. The controller then engages hold temperature mode as illustrated by part 124 once the new target temperature $T_{target}$ of 220° C. is reached. As previously mentioned, the controller may be configured to control a plurality of heating elements 23a and 23b individually, thereby controlling the temperature in a plurality of corresponding heating zones 29a and 29b. In one example, as illustrated in FIG. 13, the heater arrangement 23 includes two heating elements 23a and 23b and the heating chamber 29 comprises two heating zones 29a and 29b and the heating elements 23a and 23b operate to heat smokable material positioned within heating zones 29a and 29b respectively. In the example of FIG. 13, the controller is configured to control the operation of heating elements 23a and 23b based on temperature measurements acquired from the sensors 111a and 111b respectively.

In some examples, the controller controls the operation of multiple heating elements 23a and 23b by implementing a separate control loop/scheme for each of the heating elements 23a and 23b. In the example of FIG. 13, the controller implements the above described slope-based heater control loop for each heating element 23a and 23b using temperature measurements from the temperature sensors 111a and 111a of each respective heating element. A switch (not shown) may be provided for each of the heating elements 23a and 23b, each switch being configured to switch its respective heating element from the off state to the on state and vice versa. The controller may control each heating element 23a and 23b by controlling its respective switch in order to switch the heating elements 23a and 23b on and off. The output of each heating element's respective control loop may control the respective switches configured to control the heating elements 23a and 23b. In one example, the output of each control loop enables or disables a pin on the controller for each respective heating element 23a and 23b.

In one example, the switches that allow the controller to control the heating elements 23a and 23b are transistors or any other electronics suitable for performing the function of a switch. There may be provided a main switch that enables or disables the individual switches for each respective heating element.

Figure 14:
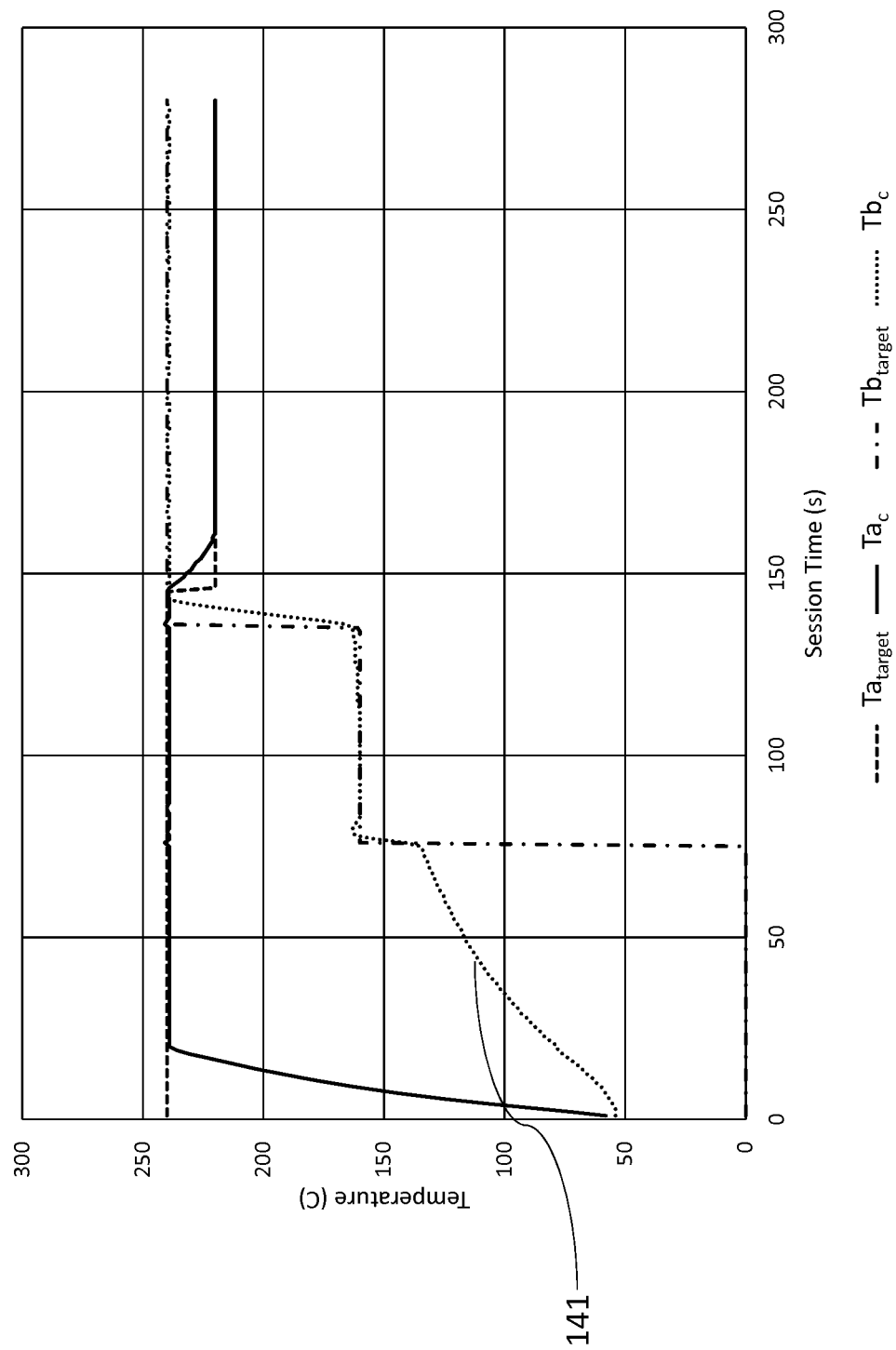
FIG. 14 shows a graph showing the time evolution of a pair of target and corresponding measured temperatures within the heating arrangement of FIG. 13.

FIG. 14 illustrates the control of the operation of two heating elements 23a and 23b by the controller. Target temperatures $Ta_{target}$ and $Tb_{target}$ may individually be set for each of the heating elements 23a and 23b. The measured current temperatures $Ta_c$ and $Tb_c$ are acquired by the controller from temperature sensors 111a and 111b associated with each of the heating elements 23a and 23b. In this example, the time evolution of set point target temperature $Ta_{target}$ and the current temperature $Ta_c$ belonging to the heating element 23a corresponding to the zone 29a is as described in relation to FIG. 12 earlier. The target temperature $Tb_{target}$ for zone 23b is initially zero; however, as indicated by part 141 of the current temperature $Tb_c$, the current temperature $Tb_c$ gradually increases while the target temperature $Tb_{target}$ remains at zero. This can be taken to be the influence of the temperature of the neighboring heating element 23a (and of zone 29a) increasing due to the element 23a's operation being controlled by the controller in order for the heating element 23a to reach the target temperature $Ta_{target}$. The current temperature $Tb_c$ of zone 29b behaves similarly to as described in the context of FIG. 12 when the target temperature $Tb_{target}$ is set to a non-zero value.

Having at least one temperature sensor 111a and 111b associated with each of a plurality of heating elements 23a and 23b of a heater arrangement 23, in order that the controller may individually control the operations of the heating elements 23a and 23b, and thereby the current temperatures $Ta_c$ and $Tb_c$ of the corresponding zones 29a and 29b respectively, based on the temperature measurements from the at least one temperature sensor 111a and 111b associated with the elements 23a and 23b, may allow better overall control of the temperature within the chamber 29 as a whole and therefore the volume of smokable material 21a being heated. Furthermore, the controller may heat the smokable material 21a along the length of the chamber 29 in controlled sequences. For example, referring to FIG. 13, the controller may operate the heating element 23a for a period of time before initiating operation of the heating element 23b. In this example, the controller may operate the elements 23a and 23b in sequence by setting a suitable target temperatures for each zone at different times.

The provision of at least one temperature sensor 111a and 111b in each of the plurality of heating elements 23a and 23b may also provide a failsafe against a runaway heating element. For example, if the temperature sensor 111a in the heating element 23a ceases to function and does not measure a value of temperature, the controller may continue to operate the heating element 23a in an attempt to reach its target temperature $Ta_{target}$. Heating element 23a could therefore be at a temperature much higher than expected, for example, the temperature of heating element 23a may exceed 240° C. In this example, the temperature sensor 111b in the neighboring heating element 23b may also detect a higher than expected temperature due to the heat from the runaway zone 23a. In one example, the controller compares the temperature measurements acquired from the temperature sensor in element 23b to temperatures expected based on the current power being supplied to the element 23b in order to determine the likelihood of a neighboring runaway heater. The controller may also perform such a comparison in order to detect other faults or unwanted conditions within the heating chamber 29.

The slope-based heater control scheme/loop may provide the advantage of not requiring the adjustment of control parameter during or between sessions of use of the smokable material heating device 1. In this regard, the slope-based heater control loop may provide a simpler and easier to implement control loop than, for example, a proportional integral derivative (PID) control loop. The simpler slope-based temperature control loop may thus provide sufficient control over temperature while being easier to set up and implement.

In an embodiment, the control circuitry 25 comprises a memory, and at least one processor configured to execute applicable method steps according to the disclosure. Furthermore, the method according to the disclosure can be implemented with one or several computer programs which can be executed by at least one processor or controller.

In an embodiment, the method steps, apparatus and the computer program according to the disclosure can be implemented by at least one separate or embedded hardware module.

The computer program(s) can be stored on at least one computer readable medium such as, for example, a memory circuit, memory card, magnetic or optic disk. Some functional entities may be implemented as program modules linked to another functional entity. The functional entities may also be stored in separate memories and executed by separate processors, which communicate, for example, via a message bus. An example of such a message bus is the Peripheral Component Interconnect (PCI) bus.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilized and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in future.

The invention claimed is:

1. A method of controlling a heater arrangement in an apparatus arranged to heat smokable material to volatize at least one component of the smokable material, the method comprising:
   implementing a heater control loop to control a heating element of the heater arrangement to heat a zone of the apparatus to a target temperature, wherein the control loop comprises, in one or more successive control periods, performing:
   determining a current temperature in the zone;
   determining a current rate of change of temperature in the zone; and
   determining a current remaining on time for the heating element of the heater arrangement to heat the zone to the target temperature based on the current rate of change of temperature, the target temperature and the current temperature of the zone.

2. The method of claim 1, further comprising:
   causing the heater arrangement to turn off the heating element that is heating the zone if the current remaining on time for the heating element expires.

3. The method of claim 2, further comprising:
   causing the heater arrangement to turn off the heating element that is heating the zone if the current remaining on time for the heating element calculated in the current control period expires during the current control period.

4. The method of claim 2, further comprising:
   in a subsequent control period to the control period during which the heating element was turned off:
   determining a current temperature in the zone and if the current temperature in the zone is less than the target temperature, turning the heating element back on and determining a current remaining on time for the heating element to heat the zone to the target temperature based on a current rate of change of temperature, the target temperature and the current temperature of the zone.

5. The method of claim 1, further comprising:
   causing the heater arrangement to turn off the heating element that is heating the zone if it is determined that the current temperature is at or above the target temperature; and
   subsequently entering a hold temperature mode.

6. The method of claim 5, further comprising:
   when in hold temperature mode, turning the heating element back on if in addition to the current temperature being at least a first temperature threshold value below the target temperature, one or more of the following conditions are also fulfilled:
   the current temperature is below the previous temperature measurement;
   a time greater than a first time threshold value has expired since the heating element was turned off, and the current temperature is at least a second temperature threshold value below the target temperature;
   a time greater than a second time threshold value has expired since the heating element was turned off, wherein the second temperature threshold value is greater than the first temperature threshold value; and
   the second time threshold value is greater than the first time threshold value.

7. The method according to claim 1, further comprising changing the target temperature during a session of use of the apparatus.

8. The method according to claim 1, further comprising determining the current temperature in the zone at first given intervals of time.

9. The method according to claim 8, wherein the control periods last for second given intervals of time, the second given intervals of time being greater than the first given intervals of time.

10. The method claim 1, wherein;
the heater arrangement comprises a plurality of heating elements, and the method further comprises:
providing at least one temperature sensor associated with each of the plurality of heating elements; and
independently implementing the method for each of the plurality of heating elements.

11. An apparatus configured to heat smokable material to volatize at least one component of the smokable material, the apparatus comprising:
a heater arrangement comprising a heating element; and
a controller configured to implement a heater control loop to control the heating element of the heater arrangement to heat a zone of the apparatus to a target temperature, wherein the control loop comprises, in one or more successive control periods:
determining a current temperature in the zone;
determining a current rate of change of temperature in the zone; and
determining a current remaining on time for the heating element to heat the zone to the target temperature based on the current rate of change of temperature, the target temperature and the current temperature of the zone.

12. The apparatus of claim 11, wherein the controller is further configured to:
cause the heater arrangement to turn off the heating element that is heating the zone if the current remaining on time for the heating element expires.

13. The apparatus of claim 11, wherein the controller is further configured to:
cause the heater arrangement to turn off the heating element that is heating the zone if the current remaining on time for the heating element calculated in the current control period expires during the current control period.

14. The apparatus of claim 12, wherein the controller is further configured to:
in a subsequent control period to the control period during which the heating element was turned off:
determine a current temperature in the zone and if the current temperature in the zone is less than the target temperature, turn the heating element back on and determine a current remaining on time for the heating element to heat the zone to the target temperature based on a current rate of change of temperature, the target temperature and the current temperature of the zone.

15. The apparatus according to claim 11, wherein the controller is further configured to:
cause the heater arrangement to turn off the heating element that is heating the zone if it is determined that the current temperature is at or above the target temperature; and
subsequently enter a hold temperature mode.

16. The apparatus according to claim 15, wherein the controller is further configured to:
when in hold temperature mode, turn the heating element back on if in addition to the current temperature being at least a first temperature threshold value below the target temperature, one or more of the following conditions are also fulfilled:
the current temperature is below the previous temperature measurement;
a time greater than a first time threshold value has expired since the heating element was turned off, and the current temperature is at least a second temperature threshold value below the target temperature;
a time greater than a second time threshold value has expired since the heating element was turned off, wherein the second temperature threshold value is greater than the first temperature threshold value; and
the second time threshold value is greater than the first time threshold value.

17. The apparatus according to claim 11, wherein the controller is further configured to change the target temperature during a session of use of the apparatus arranged to heat smokable material.

18. The apparatus according to claim 11, wherein the controller is further configured to determine the current temperature in the zone at first given intervals of time.

19. The apparatus according to claim 18, wherein the control periods last for second given intervals of time, the second given intervals of time being greater than the first given intervals of time.

20. The apparatus according to claim 11, wherein the apparatus further comprises:
a housing containing the heater arrangement; and
a mouthpiece.

21. A non-transitory computer-readable storage medium comprising a set of computer-readable instructions stored thereon, which, when executed by a processing system, cause the processing system to carry out a method of controlling a heater arrangement in an apparatus arranged to heat smokable material to volatize at least one component of the smokable material by:
implementing a heater control loop to control a heating element of the heater arrangement to heat a zone of the apparatus to a target temperature, wherein the control loop comprises, in one or more successive control periods, performing:
determining a current temperature in the zone;
determining a current rate of change of temperature in the zone; and
determining a current remaining on time for the heating element of the heating arrangement to heat the zone to the target temperature based on the current rate of change of temperature, the target temperature and the current temperature of the zone.

* * * * *